(12) United States Patent
Garuti

(10) Patent No.: US 9,511,090 B2
(45) Date of Patent: Dec. 6, 2016

(54) COMPOSITION USABLE IN THE TREATMENT OF CANCER

(76) Inventor: Eliseo Garuti, Villaviciosa-Asturias (ES)

( * ) Notice: Subject to any disclaimer, the term of this patent is extended or adjusted under 35 U.S.C. 154(b) by 102 days.

(21) Appl. No.: 13/993,686

(22) PCT Filed: Dec. 9, 2011

(86) PCT No.: PCT/IB2011/002984
§ 371 (c)(1),
(2), (4) Date: Jun. 13, 2013

(87) PCT Pub. No.: WO2012/080803
PCT Pub. Date: Jun. 21, 2012

(65) Prior Publication Data
US 2013/0287867 A1     Oct. 31, 2013

(30) Foreign Application Priority Data

Dec. 14, 2010  (EP) .................................. 10015591
Dec. 14, 2010  (IT) ......................... BO2010A000734

(51) Int. Cl.
*A61K 31/7004* (2006.01)
*A61K 33/00* (2006.01)
*A61K 9/00* (2006.01)

(52) U.S. Cl.
CPC ........... *A61K 33/00* (2013.01); *A61K 31/7004* (2013.01); *A61K 9/0019* (2013.01)

(58) Field of Classification Search
CPC . A61K 2300/00; A61K 31/7004; A61K 33/00
See application file for complete search history.

(56) References Cited

U.S. PATENT DOCUMENTS

| 3,305,446 A * | 2/1967 | Bechtol ............... A61K 9/0019 |
| | | 210/683 |
| 6,416,791 B1 * | 7/2002 | Garuti ........................... 424/722 |
| 2002/0028196 A1 * | 3/2002 | Percival ................. A61K 31/70 |
| | | 424/93.71 |
| 2006/0078629 A1 * | 4/2006 | Serfontein ..................... 424/702 |
| 2007/0191287 A1 * | 8/2007 | Yamamura et al. ............ 514/23 |

FOREIGN PATENT DOCUMENTS

| EP | 0945075 | 9/1999 |
| WO | WO 2010044070 | * 4/2010 |

OTHER PUBLICATIONS

Armand Production Company, Potassium Bicarboante, Facts, Applications & Opportunities, pp. 1-3, retrieved online Mar. 2015.*

* cited by examiner

*Primary Examiner* — Mina Haghighatian
(74) *Attorney, Agent, or Firm* — Mark M. Friedman

(57) ABSTRACT

The invention relates to a composition for use in the very rapid treatment of cell degeneration, in particular in oncologic field, characterized in that it is constituted by a compound of Potassium Bicarbonate and D-Ribose.

5 Claims, 4 Drawing Sheets

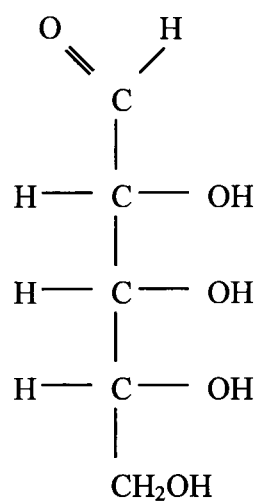
*Fig. 5*
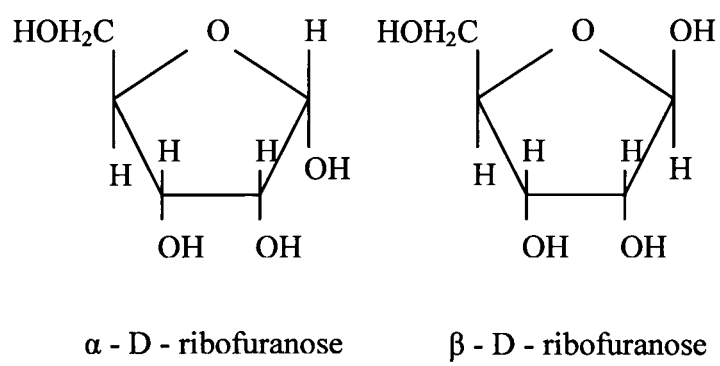
α - D - ribofuranose  β - D - ribofuranose
*Fig. 6*  *Fig. 7*

α - D - ribopyranose

β - D - ribopyranose

COMPOSITION USABLE IN THE TREATMENT OF CANCER

CROSS-REFERENCE TO RELATED APPLICATIONS

This application is a U.S. National Phase patent application of International Application Ser. No. PCT/IB2011/002984, filed on Dec. 9, 2011, and which claims the benefits of European Patent Application No. 10015591.0, and of Italian Patent Application No. BO2010A000734, both filed Dec. 14, 2010.

STATEMENT REGARDING FEDERALLY SPONSORED RESEARCH OR DEVELOPMENT

Not Applicable

BACKGROUND OF THE INVENTION (1) Field of the Invention

The present invention relates to the use of a composition as a drug for rapidly combating the tissue degeneration; in particular, the drug is particularly useful in cases of degenerative diseases caused by particular conditions of stress, such as, for example, the exposure to ionizing radiations (gamma rays and X-rays), exposure to UV, or cellular damage caused by toxic molecules, etc.

(2) Description of the Related Art

It is known that radiations in general, as well as other endogenous and exogenous factors, produce damages at the cellular level forming free radicals, highly reactive molecules which produce chemical oxidations of lipids and proteins, resulting in oxidative stress. The general effects thus produced in the organism are mainly the following: a weakening of the immune system; a stepped-up physiological organic deterioration; the production of degenerative forms.

A particularly significant example relates to the cancer induction by the radiations, mainly the ionizing radiations (X and .gamma. rays for the electromagnetic radiation, .alpha. e .beta. rays for the material particles), as was indeed highlighted by the researchers who first worked with radio-emitting materials and as has been documented by a huge amount of scientific works of the last seventy years.

A dramatic and particular example of this causal relationship between radiation exposure and increased incidence of cancer is related to the effects of radiation on healthy cells. It is known that the radiation is intended to stop the growth of a tumor, but since it is not possible to discriminate with absolute precision, in the treatment plan, the cells to be treated from the nearby healthy ones, it is necessary that the absorbed dose the system does not exceed a given value (usually indicated in 2 Gy, corresponding to 200 Rad) to prevent the irradiation of healthy tissue causes a rapid new carcinogenesis. In oncologic radiation it is known the possibility that a new cancer can develop in tissues that were directly exposed to the treatment (radiogenic pathogenesis), but it is also possible that an indirect process causes a second tumor in a different place of occurrence. It is therefore important and essential to prevent and reduce the effects of the exposure to healthy tissue during radiation therapy.

Among the effects of exposure to radiation or, in general, to oxidative stress, are to be considered the bio-physical and chemical changes that can result in damage to cell membranes and to the DNA. In fact, in the presence of an oxidizing stress, the $NA+$—$K+$ pumps do not perform its task correctly and there occurs an imbalance of the four fundamental cations for a well-balanced cellular functioning, namely Sodium, Potassium, Calcium and Magnesium. Especially in presence of degenerative diseases and in particular neoplastic forms, Sodium $NA+$ (a prevalent cation in extracellular fluids) tends to substitute Potassium $K+$ inside the cell, with a resulting serious cytoplasmic imbalance, which can conduct to a significant alteration of the intra and extra cellular acid-base conditions, to a modification of the enzyme and protein function by alteration of the binding sites for the electrolyte and a significant change of their shape. In addition, a significant decrease in the cytoplasmic concentration of Potassium can cause instability in the double helix structure of DNA and, especially, in the action of the telomerase enzyme, because the Potassium is strongly implicated in the correct structure of the G-Quadruplex (sequence of Guanine-rich nucleic acids and stabilized by K+cation), thus prompting mutagenic phenomena. It must also be taken into particular consideration the existence of a Sodium-Glucose symport (known in the literature since the 60s of last century) and recently further confirmed by MRI based on sodium ($Na.sup.23$) and performed on cancer "in vivo" compared with PET on the same tumors, completely overlapping.

BRIEF SUMMARY OF THE INVENTION

The aim of the present invention is to eliminate the above mentioned drawbacks providing with a composition to be used for achieving an effect within a short time on cellular degeneration, especially in the oncologic field, according to the characteristics of claim 1. The invention relates to the use of a composition of potassium bicarbonate and D-ribose for forming a drug, in particular an injectable drug, to be used for achieving an effect within a short time on cellular degeneration, especially in the oncologic field. Other characteristics are described in the dependent claims.

Among the advantages of the present invention, which are novel in the therapeutic field, using the drug of the present invention causes a rapid decrease, not only in the effects caused by free radicals but, above all, in the development of transformed tumor cells. The speed of action of the drug and the subsequent rapid decrease in tumor cell proliferation was seen "in vitro" on cell line A72 (canine cancer), with a slowing of proliferation with D-ribose and $KHCO.sub.3$ aqueous solution in concentration of 0.5 mM and a growth arrest in concentration of 5 mM only after 48 hours of treatment. The above combination is inventive because it is not a food supplement such as potassium ascorbate combined with ribose and administered orally, used as an antioxidant agent and as a regulator of cellular metabolism. In fact, while until now it was assumed that L-Ascorbic acid was a fundamental carrier of potassium and that the D-ribose acted in the compound as a catalyst of the process, in this case the total absence of L-Ascorbic acid and the use of only D-ribose, combined with potassium bicarbonate ($KHCO.sub.3$), represents an absolute innovation in therapy. Up to this point, it has never been taken into account that this monosaccharide could salify an alkali metal such as potassium to form the compound potassium ribosate. This compound has characteristics of specificity, which is a crucial issue in a therapeutic context, as it acts on cells that have undergone degenerative changes especially in oncological sense, while leaving healthy cells unaffected.

This drug combines the functional characteristics of its components resulting in extremely fast results that are not comparable with respect to using the components individually (e.g. an injectable drug made from potassium chloride and another ribose based drug, even injectable, when administered separately, did not produce the same effect); the drug is not toxic (at prescribed doses) and can be used for long periods (months and even years) without damage.

BRIEF DESCRIPTION OF DRAWINGS

Every technician who works in this field will better understand these advantages and features and other advantages and features of the present invention thanks to the enclosed figures that relate to preliminary results of the effects of the drug on human cells.

FIGS. 5, 6, 7, 8, 9 relate to configurations of D-ribose.

DETAILED DESCRIPTION OF THE INVENTION

The following description illustrates the preliminary results of the effects of D-ribose and $KHCO_3$ in an aqueous solution on HTB125 irradiated with X-ray.

In particular, the study was directed to the effects of D-r-ribose and $KHCO_3$ in an aqueous solution on normal human breast cells HTB125 irradiated with X-ray.

As mentioned above, the radiotherapy can generate secondary tumors (radiogenic pathogenesis) in the same radiation seat or in other seats. It is therefore important and essential to prevent and reduce the effects of exposure to healthy tissue during radiation therapy.

Materials and Methods

HTB125 cells of mammary gland not tumoral were purchased from American Type Culture Collection (ATCC)—Manassas, Va., U.S.A. The cells were maintained in DMEM (Dulbeccos's Modified Eagle's Medium) purchased from Lonza to which are added 10% fetal calf serum (Lonza), 1% L-glutamine (Sigma Aldrich), 1% Penicillin -Streptomycin (Sigma Aldrich) and 30 .mu.g/ml of epidermal growth factor (Gibco). The cells were incubated at 37.degree. C. in a humidified atmosphere with 5% CO2. The D-ribose was purchased from Sigma-Aldrich and potassium bicarbonate from BDH Prolabo. A stock solution (K:D-rib) 250 mM was prepared by dissolving 0.15 mg of D-ribose and 0.3 mg of $KHCO_3$, the whole being stirred until the $CO_2$ is completely released into the air.

The cells were maintained by changing the culture media every 48 hours.

The cell population was splitted when it reaches 90-100% of confluence. Trypsin (Sigma Aldrich) was used to split the cell cultures that reached confluence. This enzyme acts as a protease capable of separating the links between cell and substrate as well as cell-cell links.

Treatment and Irradiation of Cell Cultures

The day before irradiation, cells were seeded 8000/ml and treated with a solution of 5 mM (K:D-rib). The solution was obtained by diluting the stock 250 mM (K:D-rib) in DMEM. On the day after seeding, cells were irradiated.

Figure 1:
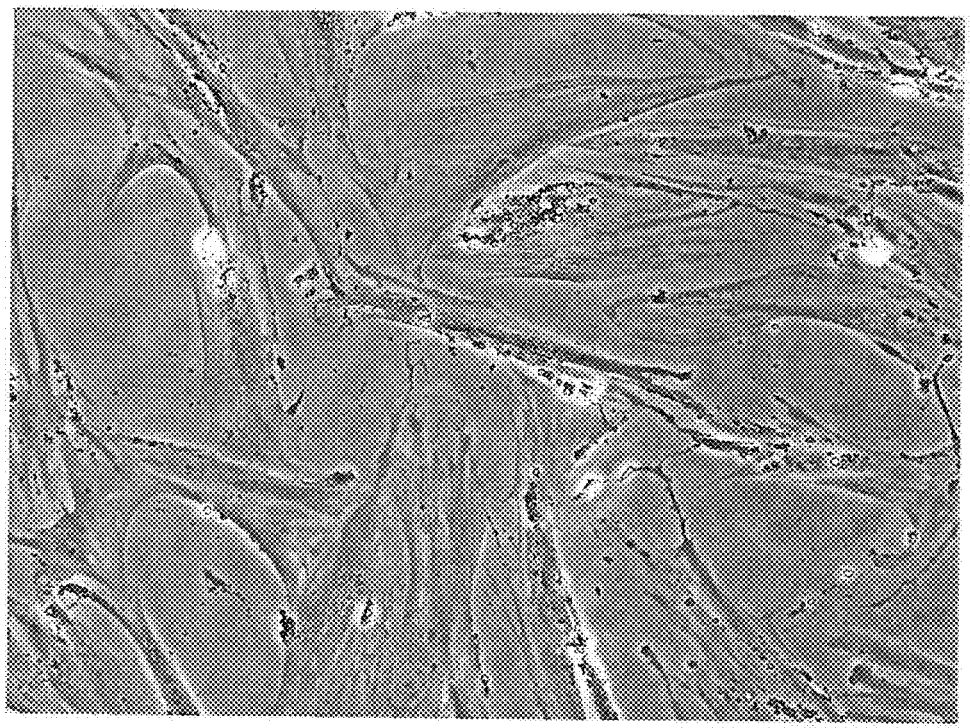
FIG. 1 relates to a photo of a control sample.
Figure 2:
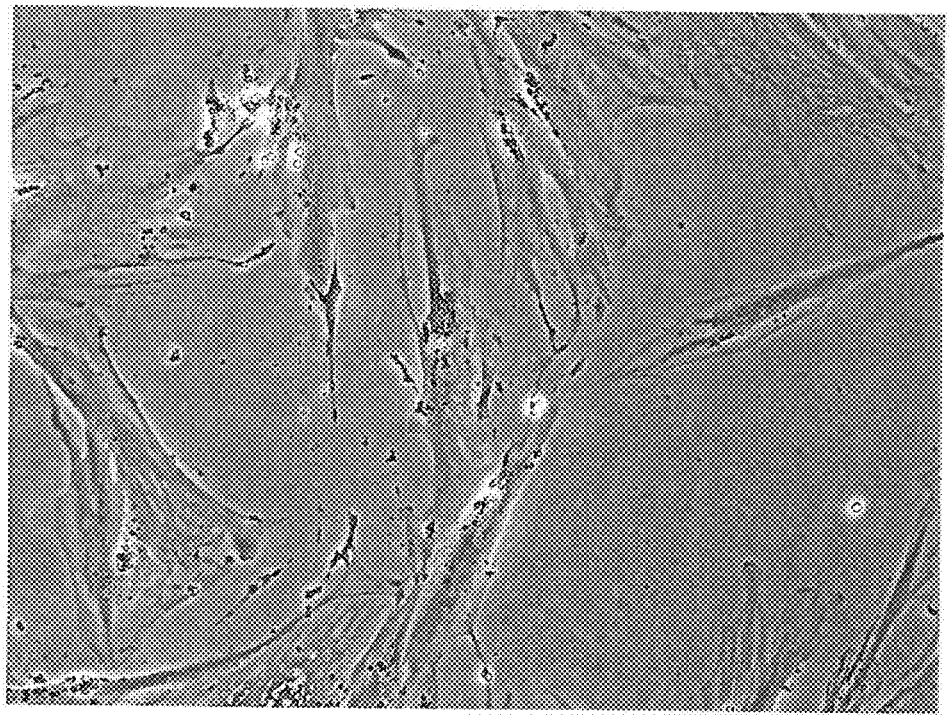
FIG. 2 relates to a photo of a control sample irradiated with X-ray.
Figure 3:
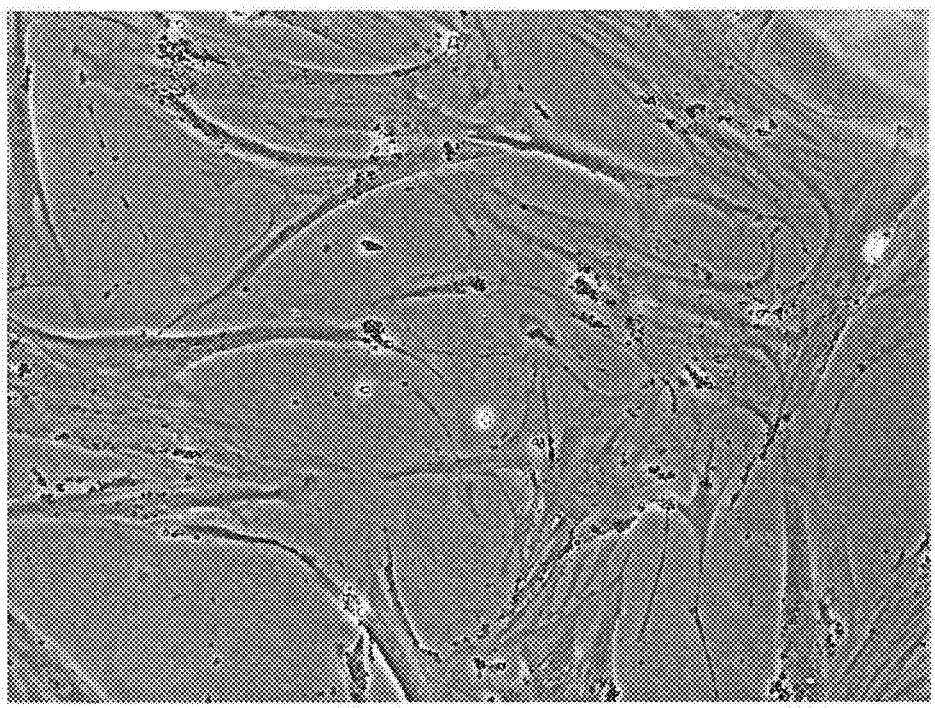
FIG. 3 relates to a photo of a sample treated with the drug of the present invention and irradiated with X-ray.
Figure 4:
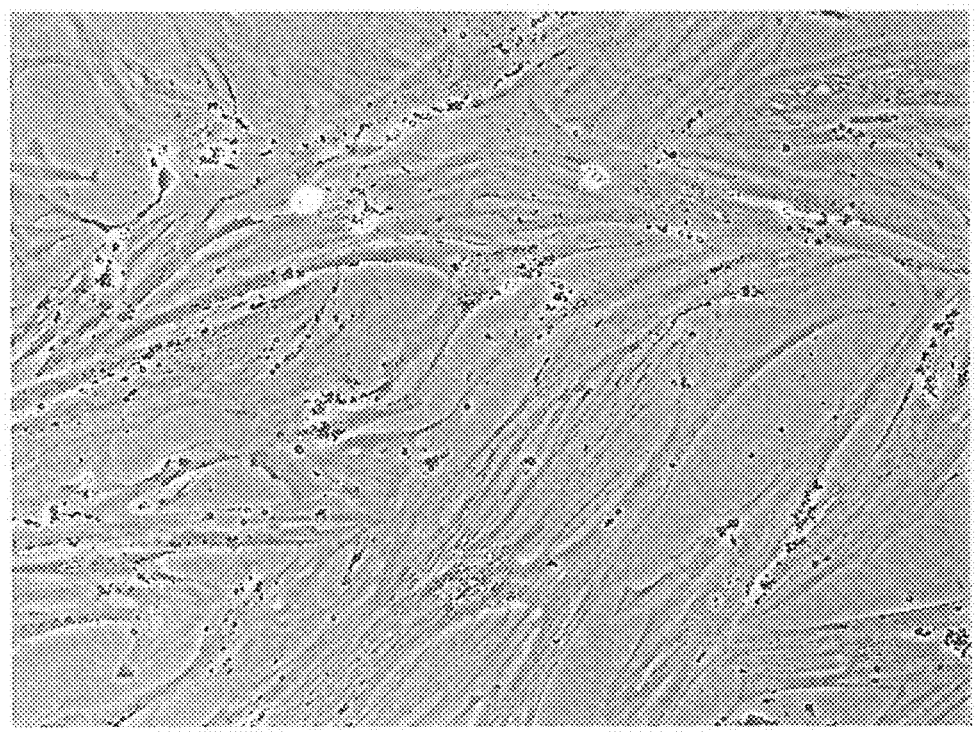
FIG. 4 relates to a photo of a sample treated with the drug of the present invention and not irradiated.

In particular, four samples were prepared: control (C, shown in FIG. 1), irradiated control (C_irr, shown in FIG. 2), treated non-irradiated (Krib, shown in FIG. 4) and treated irradiated (Krib_irr, shown in FIG. 3). The irradiation was performed with an X-ray tube (Faxitron cabinet 43855D) by placing the Petri dish on a rotating plate for ensuring uniformity of dose. The X-ray tube was set to 106 kV and 3 mA. The dose was equivalent to 1.01 Gy/min and the radiation occurred for a time of 2 min. The evaluation of the absorbed dose was carried out via the system Victoreen NERO mAx Model 8000. In addition, the dose was measured by simulating the Petri system covering the sensor with the cover of the same Petri dish. On the day after irradiation, means of treated and untreated samples have changed. The treatment was carried out until the end of the experiment.

Results—Discussion

To study cell growth and the effect of treatment, the cell growth was controlled and in particular, the time between irradiation and the first split, i.e. the attainment of confluence was controlled. Samples C, Krib and Krib_irr have reached 90% confluence after 7 days after sowing while the sample C_irr 10 days after sowing. In addition, the use of trypsin was much less effective in the samples C, Krib and Krib_irr, compared to the sample C_irr. These results show that the samples C, Krib and Krib_irr have the same growth kinetics. The kinetics in Krib_irr treated with 5 mM (K:D-rib) was not altered by the radiation; on the contrary the sample C_irr has reached the confluence with a significant delay of 3 days. Considering the difference in efficacy of trypsin, it can be assumed a protective effect of the solution (K:D-rib) on not tumoral cells HTB125 treated before irradiation and subsequently the same.

The drug of the invention, which in its form of administration is injectable, consists of a mixture of potassium bicarbonate ($KHCO_3$) and an aldopentose that includes D-ribose ($C_5H_{10}O_5$). The compound obtained from these two molecules, which is called potassium ribosate, is water soluble and it is administered by injection.

It was not shown before that the composition which constitutes the drug of the present invention is administered intramuscularly or intravenously, nor are known other trials that suggest the injection of a drug with potassium bicarbonate and D-ribose components. Results are surprising and rapid in the prevention and treatment of degenerative diseases.

It is known that D-ribose is a pentose sugar which plays a key role in energy metabolism of the cell (primary component for the production of ATP—adenosine triphosphate) and as a precursor in the biosynthesis of RNA (ribonucleic acid) and, in the form of deoxyribose, DNA (deoxyribonucleic acid). The. D-ribose is thus simple but it is a compound of fundamental importance in metabolic and functional pathways of the cell (especially at the level of production, conversion and use of energy). Precisely in this sense, the mechanisms involved in the Krebs cycle acquire a particular importance. The D-ribose reveals an active role in some organic co-factors and its wide distribution in the forms of life on our planet suggests that it may have been involved in prebiotic chemistry on Earth.

The D-ribose, in addition to the open-chain form (FIG. 5) has other four isomeric configurations: .alpha. and .beta.

Figure 8:
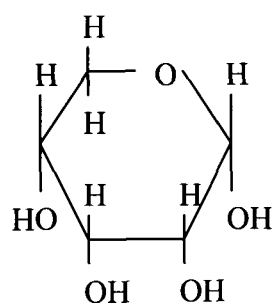
Figure 9:
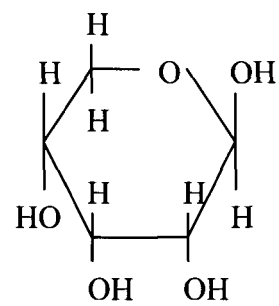

D-ribopyranose (FIGS. 6 and 7), .alpha. and .beta. D-ribofuranose (FIGS. 8 and 9). In living systems ribose is present in the form .beta. D-ribofuranose, and the open-chain form is able to mediate between the other three closed-chain structures for converting such structures and promoting the dextrorotatory isomeric .beta. ribofuranose structure.

D-ribose and the potassium bicarbonate of the present invention are in pure microcrystalline form, readily soluble in water for forming injectable solutions; the compound is very unstable because of its easy oxidizability and must be stored in suitable protected mono-dose containers.

D-ribose salifies with potassium bicarbonate in cold aqueous solution forming the compound called potassium pibosate. Until now this aspect, i.e. the ability of the D-ribose to form a salt, has been completely overlooked by the scientific community because it was considered a marginal issue. This effect is made possible thanks to the action of the molecule in the form of open-chain which, in aqueous solution, linking two potassium ions and involving rotation to close a ring, that gives stability and continuity to the .beta. D-ribofuranose form.

Its action has no toxicity (at prescribed doses) and can be used for indeterminate time. It acts rapidly to contrast the uncontrolled proliferation of cells that have undergone neoplastic degeneration, acting on the mechanisms related to the energy metabolism of these cells, reducing the effect of oxidative stress, enhancing the activity of the immune system and maintaining or restoring the concentration of intracellular potassium to the correct values.

To better understand these statements it is necessary to remember that the importance of the pyrrole rings for plant and animal life is known in scientific literature, both in the chemical and in the bio-medical field, since the end of 1800 and until the early decades of last century (thanks to the works of Italian Luigi Giacomo Ciamician, born in Trieste in 1857 and died in Bologna in 1922). In the 40s of last century, Niels Troensegaard developed a hypothesis (improperly called "Pyrrole Troensegaard's Hypothesis," as reported in the appendix by the author of "On the Structure of the Protein Molecule", Acta Chemica Scandinavica, 1 [1947]:672-682). This hypothesis is still controversial, according to which the exact presence of heterocyclic units of pyrrolic type constitutes the ground for the structure of proteins. This is also true in the structure of ribonucleic acid (RNA), in which the presence of pyrrolic rings in the helical structure is highlighted by Purines (Adenine and Guanine).

The heme groups of hemoglobin and chlorophyll contain an iron ion and a magnesium ion bound in a heterocyclic structure known as porphyrin, which consists of four pyrrolic rings linked together and with the ion (iron or magnesium) in the center of the structure. Also some amino acids (histidine, proline, tryptophan, pyrrolysine) contain a pyrrolic ring in their structure. It is also important to note that the black pigments, skin, hair, moles, etc., are in close relationship with the blacks of Pyrrole and this allows to formulate the hypothesis that these compounds are oxidized and poly-condensed pigments with pyrrolic structure.

It is important to note that the imidic Hydrogen present in the structure of Pyrrole is easily replaced by the potassium cation (salification process) but not by the sodium cation (Ciamician effect, which occurs in a slightly acidic environment), although these elements are similar in physico-chemical terms. But, when the local environment undergoes a change in pH, from neutral or slightly acidic to slightly alkaline, the sodium can bind to the nitrogen of NH group thus triggering the distortion and the opening of the ring. When the process of carcinogenesis begins, the pyrrolic groups seem to be inactivated precisely by an imbalance Sodium/Potassium with changes in acid-base conditions. Furthermore, the mechanisms that underlie the transformation of the cells with carcinogenic effect lies in the polymerization of RNA which is a key in opening the pyrrole rings of purines.

As pyrrole, thiophene and furan are similar to each other; during the formation of these compounds, all three follow the rule of the similarities of Angeli. It is therefore reasonable to think that during the process of biologic synthesis of protein derivates of such compounds, similar physico-chemical reactions take place and that, in particular conditions, a pyrrolic group can be replaced by a tiofene or furanose group.

Potassium ribosate contains in its molecule a furanose group that can, by analogy, replace one of the pyrrole groups in potassiun hemoglobinate or potassium proteinate.

Thus potassium pibosate, reactivating (by analogy) the pyrrole group, restores the phenomena of cell auto-synthesis structuring to physiologic normality. This is even more important with respect to RNA level because it can limit its uncontrolled polymerization (as neoplastic cells have a gene overexpression and are often multinucleated). These biochemical-physical mechanisms, activated by the compound of the present invention and which occur in the cell cytoskeleton, play a key role in inhibiting the uncontrolled proliferation; also, this interpretation with respect to the action of D-ribose is the key for the absolute innovation of this invention.

Moreover, since the salification is a reversible process, the potassium pibosate carried by hemoglobin, by entering the cell, restores the balance between the intermolecular forces of peptide groups present within the cell and restores the concentration of intracellular potassium to the correct values.

This compound has therefore characteristics of specificity, since it is able to act on cancer cells to counter their uncontrolled replication, but at the same time acts of normal cells to maintain their proper electrolyte and electrochemical balance, without creating to the latter any kind of injury in the mechanisms of metabolic regulation, but rather correcting functional imbalances. The results of inhibiting of the development of degenerative processes are achieved within a very short time which is surprising. It is therefore a very valuable and very strong cellular antioxidant, which combines together the features of the D-ribose and potassium, providing a much more active compound than when the two constituents taken separately. It is evident the synergistic effect of the composition of the invention is achieved when it is used as an injectable drug.

It emerges from stoichiometric calculations that the proportion between potassium bicarbonate and ribose must be of a 2:1 ratio, but it is possible to have a 3:1 relation.

Regarding the storage and the dosage, the compound of potassium ribosate must be protected from humidity and the sun's rays and dosed in injectable vials or other suitable separated containers for preparing an extemporary solution of very pure D-ribose and bicarbonate of potassium according to the following preferable proportions. The proportions provide to use an injectable vial of potassium bicarbonate and D-ribose containing two doses of first component and one dose of the second component. It is also possible to use three doses of potassium bicarbonate and one dose of D-ribose. Furthermore, it is possible to use an injectable vial of potassium bicarbonate containing two doses of this component and an injectable vial of D-ribose containing one dose of the same. It is also possible to use four doses of potassium bicarbonate and one dose of D-ribose. In practice, the details may still vary in an equivalent amount, percentage, type of components used, without going beyond the scope of the idea of the solution adopted and therefore remaining within the limits of the protection afforded by this patent.

The invention claimed is:

1. A method for reducing the effects of exposure of radiotherapy to healthy tissue, comprising:
   exposing a subject to radiotherapy, and
   intramuscularly injecting a therapeutically effective amount of a composition comprising potassium bicarbonate and D-ribose to subject.

2. The method according to claim 1, wherein said potassium bicarbonate and D-ribose are in a ratio of 2:1.

3. The method according to claim 1, wherein said potassium bicarbonate and D-ribose are in a ratio of 3:1.

4. The method according to claim 1, wherein said potassium bicarbonate and D-ribose are in a ratio of 4:1.

5. The method according to claim 1, wherein prior to said injecting, each of said potassium bicarbonate and D-ribose is in a single dose, and is associable at the time of use.

* * * * *

UNITED STATES PATENT AND TRADEMARK OFFICE
CERTIFICATE OF CORRECTION

PATENT NO.         : 9,511,090 B2                                      Page 1 of 1
APPLICATION NO.    : 13/993686
DATED              : December 6, 2016
INVENTOR(S)        : Eliseo Garuti It is certified that error appears in the above-identified patent and that said Letters Patent is hereby corrected as shown below:

Claim 1, Column 7 should be corrected as follows:
Line 13: Change:
-- D-ribose to subject --
to
"D-ribose to said subject"

Signed and Sealed this
Eighteenth Day of April, 2017

Michelle K. Lee
*Director of the United States Patent and Trademark Office*